US010921212B2

(12) United States Patent
Backman et al.

(10) Patent No.: US 10,921,212 B2
(45) Date of Patent: Feb. 16, 2021

(54) AUTOMATED CALIBRATION SYSTEM FOR A FIBER OPTIC PROBE

(71) Applicants: NORTHWESTERN UNIVERSITY, Evanston, IL (US); AMERICAN BIOOPTICS, LLC, Chicago, IL (US)

(72) Inventors: Vadim Backman, Chicago, IL (US); Bradley Gould, Evanston, IL (US); Nikhil Mutyal, Foster City, CA (US); Frank Garrett, Jr., Barrington, IL (US); The Quyen Nguyen, Evanston, IL (US); Michael Garrett, Wilmette, IL (US)

(73) Assignees: NORTHWESTERN UNIVERSITY, Evanston, IL (US); AMERICAN BIOOPTICS, LLC, Chicago, IL (US)

( * ) Notice: Subject to any disclaimer, the term of this patent is extended or adjusted under 35 U.S.C. 154(b) by 0 days.

(21) Appl. No.: 16/011,034

(22) Filed: Jun. 18, 2018

(65) Prior Publication Data

US 2018/0368691 A1 Dec. 27, 2018

Related U.S. Application Data

(60) Provisional application No. 62/520,829, filed on Jun. 16, 2017.

(51) Int. Cl.
*A61B 5/00* (2006.01)
*G01N 21/47* (2006.01)
*G01M 11/08* (2006.01)

(52) U.S. Cl.
CPC ......... *G01M 11/088* (2013.01); *A61B 5/0075* (2013.01); *A61B 5/0084* (2013.01); *G01N 21/474* (2013.01); *G01N 21/4785* (2013.01); *A61B 2560/0233* (2013.01); *G01N 2021/4742* (2013.01)

(58) Field of Classification Search
CPC ............. G01N 21/474; G01N 21/4785; G01N 21/278; G01N 2021/4742; A61B 2560/0233; A61B 5/1495; G01M 11/088
See application file for complete search history.

(56) References Cited

U.S. PATENT DOCUMENTS

| 4,990,770 A * | 2/1991 | Hemmann | G01M 11/31 250/227.24 |
|---|---|---|---|
| 5,367,401 A * | 11/1994 | Saulietis | G01N 35/00029 356/246 |
| 5,375,179 A * | 12/1994 | Shaar | G02B 6/3803 382/204 |
| 5,852,494 A * | 12/1998 | Skladnev | A61B 5/1495 356/243.1 |
| 10,041,831 B2 * | 8/2018 | Hasegawa | A61B 5/0261 |
| 2003/0058450 A1 * | 3/2003 | Mosley | G01N 21/3151 356/436 |

(Continued)

*Primary Examiner* — Maurice C Smith
(74) *Attorney, Agent, or Firm* — Nixon Peabody LLP

(57) ABSTRACT

An automated calibration system that includes a probe guide and a target assembly. The probe guide receives an optical probe, and the target assembly includes one or more calibration targets. The target assembly is slideable relative to the probe guide so that a first calibration target is aligned under the optical probe in a first position of the target assembly and a second calibration target is aligned under the optical probe in a second position of the target assembly.

12 Claims, 5 Drawing Sheets

(56) References Cited

U.S. PATENT DOCUMENTS

| | | | | |
|---|---|---|---|---|
| 2009/0147355 A1* | 6/2009 | Jennings | ................ | G02B 21/26 |
| | | | | 359/391 |
| 2013/0235369 A1* | 9/2013 | Koifman | ................ | G01M 11/31 |
| | | | | 356/73.1 |
| 2014/0022631 A1* | 1/2014 | Hunnell | ................ | G02B 21/34 |
| | | | | 359/396 |

* cited by examiner

AUTOMATED CALIBRATION SYSTEM FOR A FIBER OPTIC PROBE

This invention was made with government support under grant no. R01 CA128641 awarded by the National Institutes of Health. The government has certain rights in the invention.

BACKGROUND

Currently, there are devices available for minimally invasive in vivo diagnostic or therapeutic procedures. Many of these devices include systems with fiber optic probes to transmit light to and from the tissue. More specifically, the fiber optic probes transmit broadband or a laser light to a target tissue with a first optical fiber, and light that is elastically scattered is received with a second optical fiber. The received light is then channeled to a receiver, and the spectrum of the signal is recorded.

Low-coherence enhanced backscattering (LEBS) spectroscopy is an angular resolved backscattering technique that is sensitive to sub-diffusion light transport length scales. Thus, LEBS probes preserve information about scattering phase function and depth-limited interrogation (superficial depths).

The majority of precancerous structural changes in patients occur in the mucosal layer of tissue. These structural changes can be quantified by measuring changes in the depth-limited optical properties of the mucosal layer. LEBS probes measure depth-resolved optical properties with sensitivity to sub-diffusion length scales. Thus, LEBS probes are beneficial to determine precancerous colon cells, as well as other types of cancerous cells.

Exemplary probes are used for optically determining a target for tumors or lesions using what is referred to as "Early Increase in microvascular Blood Supply" (EIBS) that exists in tissues that are close to, but not themselves, the lesion or tumor. Exemplary probes are also used to screen for possibly abnormal tissue using LEBS. While the abnormal tissue can be a lesion or tumor, the abnormal tissue can also be tissue that precedes formation of a lesion or tumor, such as precancerous adenoma, aberrant crypt foci, tissues that precede the development of dysplastic lesions that themselves do not yet exhibit dysplastic phenotype, and tissues in the vicinity of these lesions or pre-dysplastic tissues.

For more details on an optical probe assembly, see, for example, U.S. patent application Ser. No. 11/604,659 (published as U.S. Patent Application Publication No. 2007/0129615), U.S. patent application Ser. No. 12/684,837 (published as U.S. Patent Application Publication No. 2010/0262020) and U.S. patent application Ser. No. 13/963,560 (published as U.S. Patent Application Publication No. 2014/0036271), the disclosures of which are incorporated by reference in their entireties.

SUMMARY

This application is directed toward an automated calibration system for a fiber optic probe. The calibration system provides quality insurance of the fiber optic probe, and thus increases treatment success with the fiber optic probe. In some embodiments, the automated calibration system is used with a LEBS probe. The automated calibration system may remove uneven field illumination, and thus the automated calibration system provides improved data accuracy, ease of use, and stability.

The disclosed embodiments include a probe guide and a target assembly. The probe guide receives an optical probe, and the target assembly includes one or more calibration targets. The target assembly is slideable relative to the probe guide so that a first calibration target is aligned under the optical probe in a first position of the target assembly and a second calibration target is aligned under the optical probe in a second position of the target assembly.

The disclosed embodiments include a method of calibrating an optical probe. The method includes mounting a probe within a probe guide, sliding a target assembly relative to the probe guide so that a first calibration target is aligned under the optical probe, and projecting light on the first calibration target. Additionally, the method includes sliding the target assembly relative to the probe guide so that a second calibration target is aligned under the optical probe and projecting light on the second calibration target.

DETAILED DESCRIPTION OF EMBODIMENTS

Figure 1A:
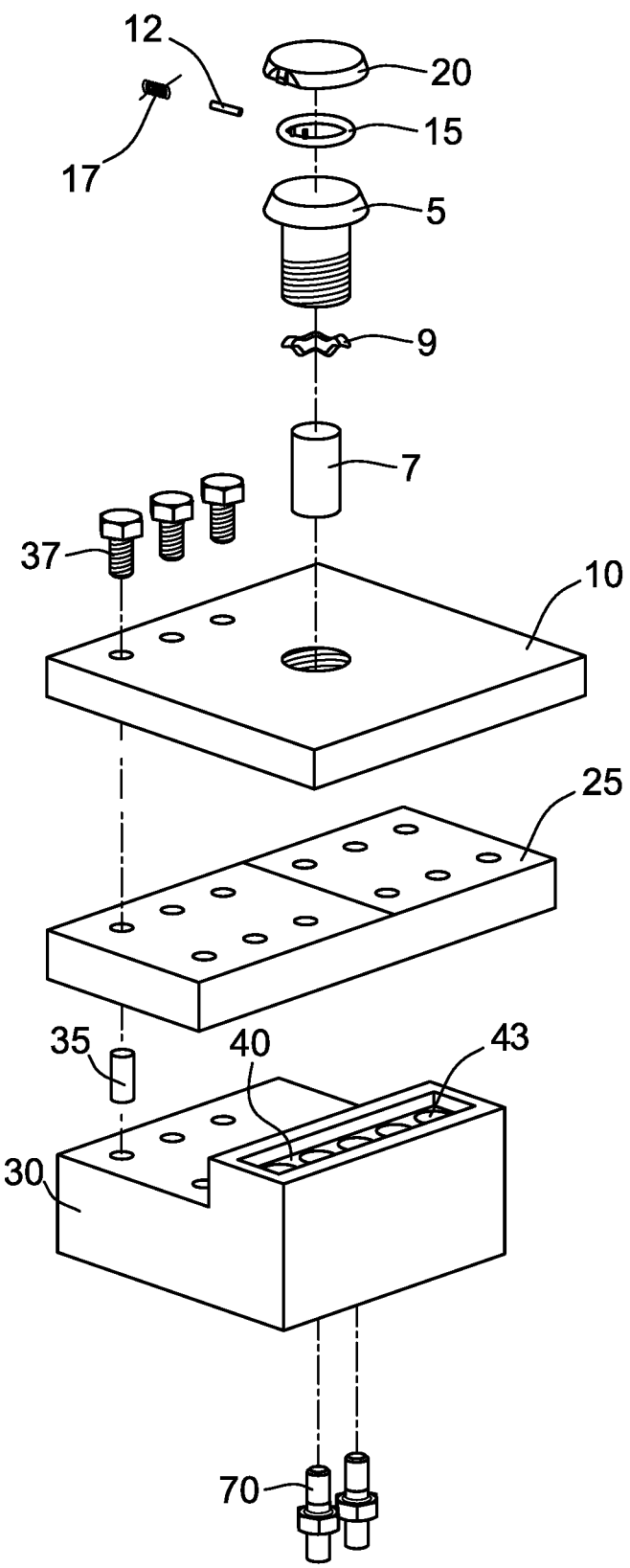
FIGS. 1A and 1B illustrate a calibration system in accordance with the present disclosure, where FIG. 1A provides an exploded view.
Figure 1B:
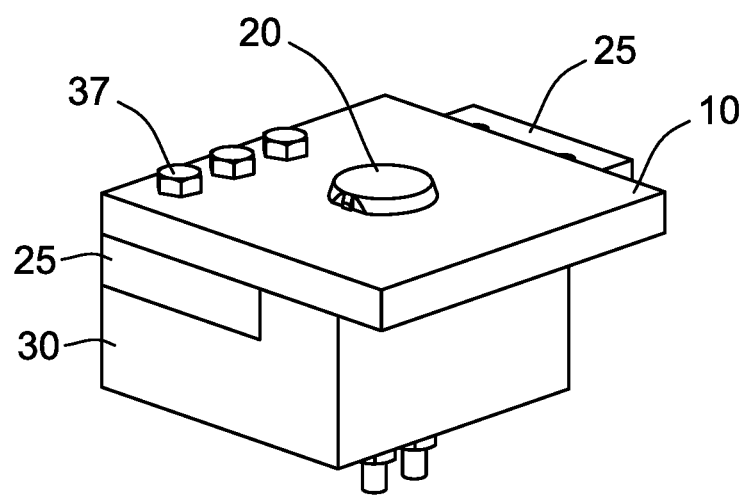

As shown in FIGS. 1A and 1B, an exemplary embodiment of an automated calibration system 1 with a manually operated lid 20 includes a probe mount 5 and a probe guide 7 attached to a mounting base 10. Probe mount 5 and probe guide 7 may each be a cylindrical member configured to receive an optical probe, such as a LEBS probe. Probe mount 5 may be disposed over and around probe guide 7 when assembled. Additionally, as shown in FIGS. 1A and 1B, probe mount 5 may include screw-like threads and rivets so that it may be removably attached to mounting base 10. A washer 9 may attach probe mount 5 to probe guide 7.

In some exemplary embodiments, probe mount 5 may be attached to a cap retainer 15 and a lid 20. Cap retainer 15 may include a calibration hinge pin 12 and a wire torsion spring 17, as discussed further below. Lid 20 may be disposed over probe mount 5. As shown in FIG. 1A, both cap retainer 15 and lid 20 may include disk-like members so that an optical probe may be disposed within and through cap retainer 15, lid 20, probe mount 5, and probe guide 7.

Mounting base 10 may be attached to a positioning stage 25 with, for example, one or more screws 37. Furthermore, positioning stage 25 may be attached to a target assembly 30 with, for example, one or more screws 37. Additionally, a spring pin 35 may be disposed between mounting base 10 and positioning stage 25 to help secure mounting base 10 to positioning stage 25.

Lid 20, cap retainer 15, probe mount 5, and/or probe guide 7 may be formed of a metal material including, for example, stainless steel, aluminum, or high-carbon steel. In other embodiments, lid 20, cap retainer 15, probe mount 5, and/or probe guide 7 may be formed of plastic and/or glass. In some embodiments, lid 20, cap retainer 15, probe mount 5, and probe guide 7 may be formed of the same or differing materials.

Figure 2A:
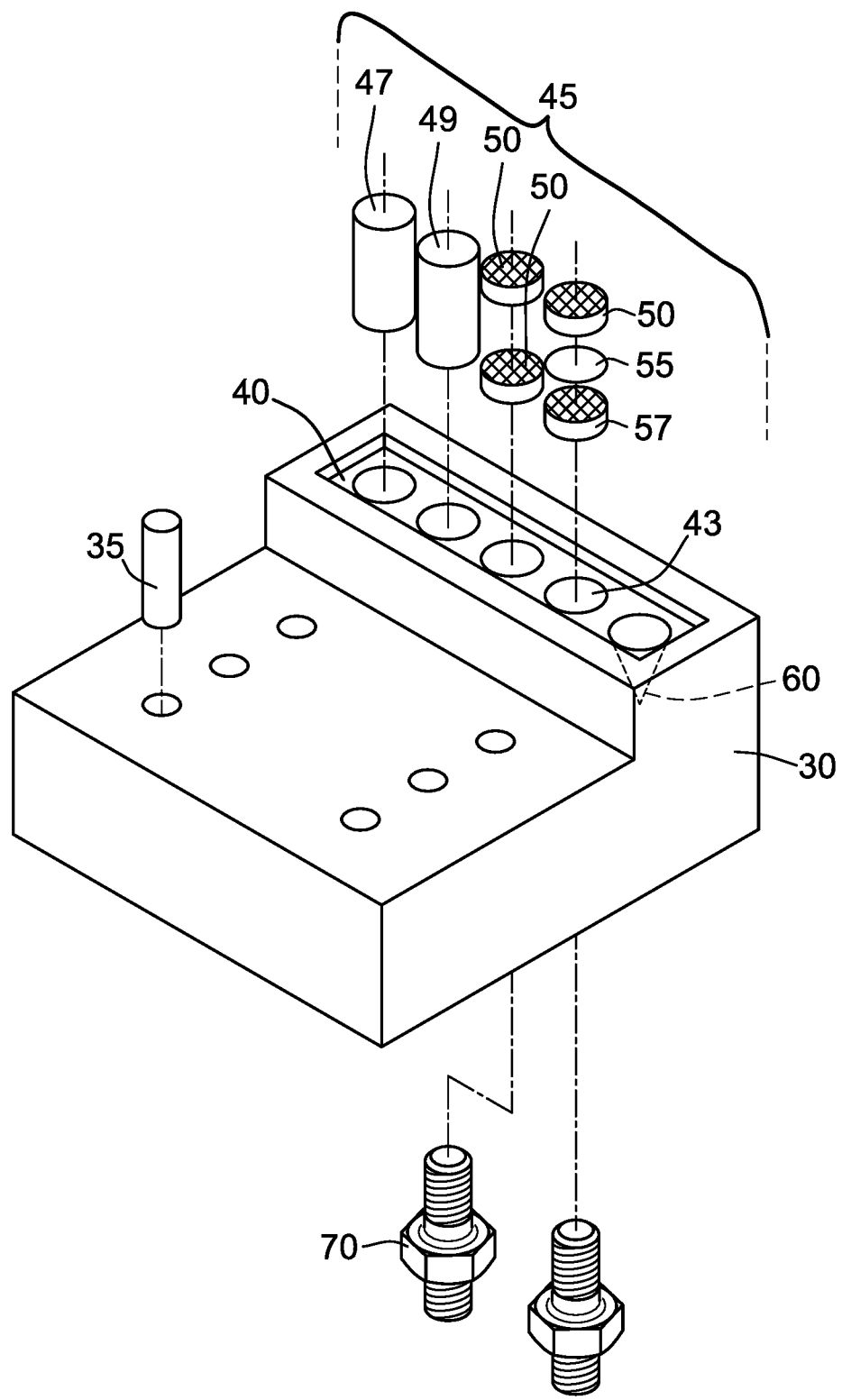
FIGS. 2A and 2B illustrate a target assembly of the calibration system in accordance with the present disclosure, where FIG. 2A provides an exploded view.
Figure 2B:
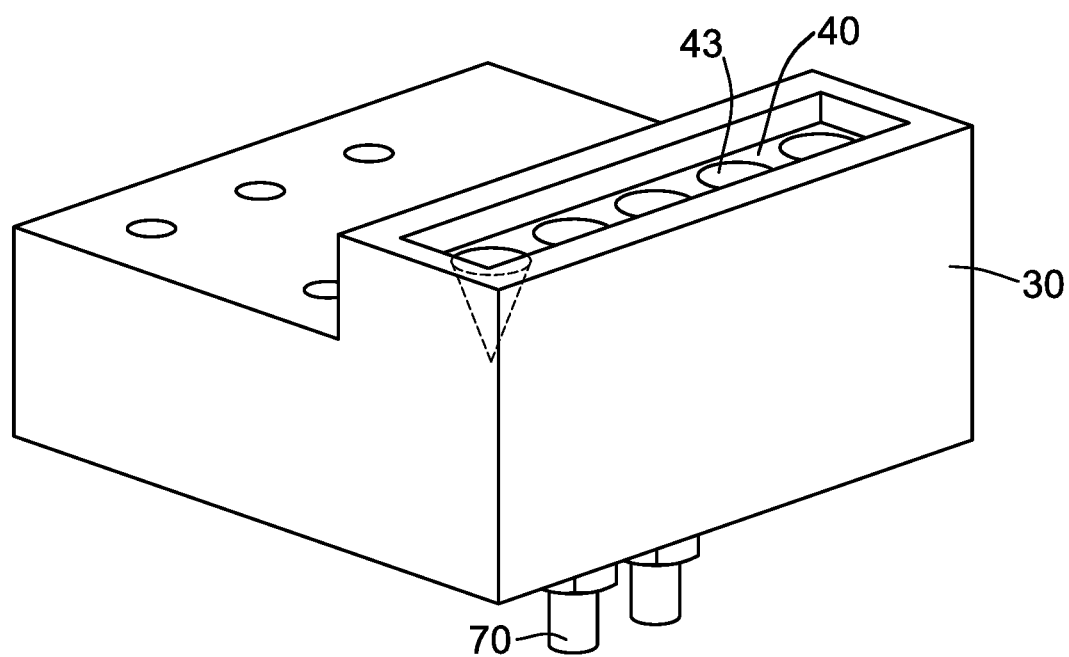

As shown in FIGS. 2A and 2B, target assembly 30 includes a target base 40 with one or more recesses 43, where target base 40 forms a recessed well. One or more calibration targets 45 may be disposed in recesses 43. For example, five calibration targets 45 may be disposed in target base 40. However, it is also envisioned that more or less calibration targets 45 may be disposed in target base 40. The number of recesses 43 may be equivalent to the number of calibration targets 45. As shown in FIGS. 2A and 2B, calibration targets 45 may include optical filters of phantom, white, flat field, mercury argon, and/or black.

The phantom calibration target may include a phantom plug 47. In some embodiments, phantom plug 47 may include a material with optical backscattering and/or light propagation properties similar to that of human tissue. Thus, for example, the backscattering and/or light propagation properties of phantom plug 47 may mimic those of healthy or diseased tissue (pre-cancerous or cancerous tissue). Phantom plug 47 may be made of, for example, silicone, polyurethane, or other similar elastomeric materials known to one of skill in the art. The material of phantom plug 47 may be compounded with varying degrees of titanium dioxide (or a similar scattering agent) in order to achieve the desired optical backscattering and/or light propagation properties. Additionally or alternatively, the material of phantom plug 47 may include one or more dyes in order to achieve a desired spectral shape. The white calibration target may include a white standard plug 49. In some embodiments, white standard plug 49 may be a diffuse reflectance intended for intensity calibration of a light source in a desired wavelength range. For example, in some embodiments, the desired wavelength range may be within the visible wavelength range. White standard plug 49 may be made of, for example, PTFE or other similar optically lambertian materials.

Figure 3:
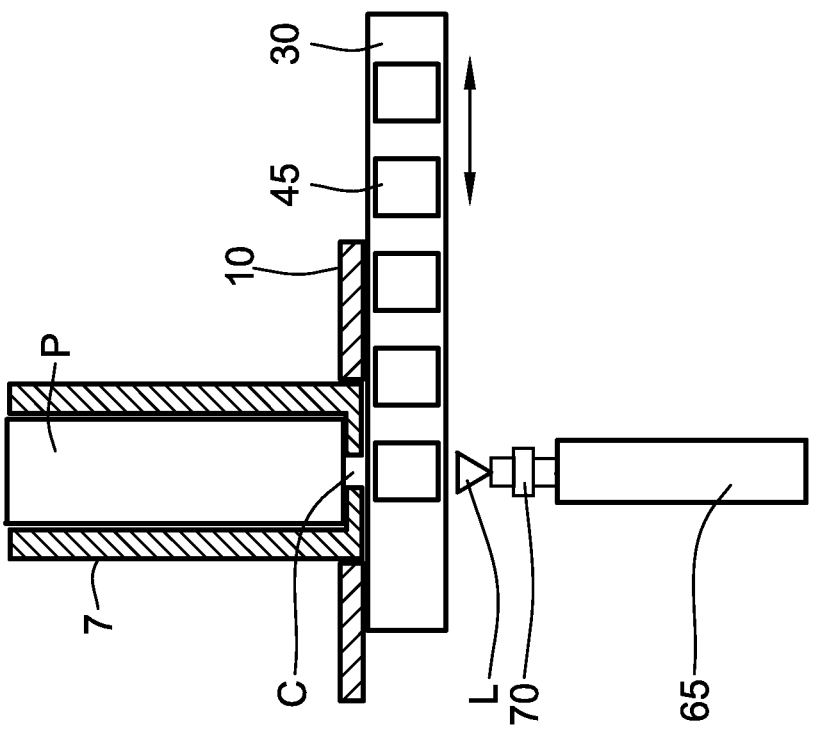
FIG. 3 illustrates the calibration system in accordance with the present disclosure.

The flat field calibration target may include a diffuser 50. In some embodiments, diffuser 50 may include a reflective diffuse material or a transparent diffuse material. The transparent diffuse material may be coupled to a light source (not shown). Diffuser 50 may be used to calibrate individual throughput of optical collection elements in optical probe P (FIG. 3). Exemplary reflective materials of diffuser 50 may include, for example, ground glass with a metal coating. Exemplary transparent materials of diffuser 50 may include, for example, glass (with a diffuse surface), ground glass, and other similar optically diffusing materials.

The mercury argon calibration target may include a neutral density filter 55 and a UV filter 57. Neutral density filter 55 may be used to control (e.g., lower) the intensity of a mercury argon calibration light source to prevent optical saturation of detection. UV filter 57 may be used to provide even wavelengths and/or to selectively control wavelength intensity.

The black calibration target 60 may include an adhesive black paper. In some embodiments, the black calibration target includes an optically absorbing material that prevents back reflection and that provides a surface against which optical probe P may be calibrated for internal reflections. The optically absorbing material may include an optically absorbing surface with a water medium, or may include an optically absorbing surface with a solid non-water medium having a refractive index substantially similar to that of water. The black calibration target may be made of, for example, an optically absorbing cloth or a similar non-reflective material. The shape of the black calibration target may be any shape designed to redirect any non-absorbed light (i.e., partially reflected light) away from the optical elements of optical probe P.

As shown in FIG. 3, when assembled, an optical probe P may be disposed within probe mount 5 and probe guide 7. In some embodiments, optical probe P is an LEBS probe. Mounting base 10, positioning stage 25, and target assembly 30 may be disposed under optical probe P. Target assembly 30, including calibration targets 45, may be moveable with regard to probe P. Thus, a first calibration target may be disposed in position C such that the first calibration target is disposed directly under probe P. Then, target assembly 30 may be slid in a direction perpendicular to probe P so that a second calibration target is disposed in position C. Target assembly 30 may be sufficiently lubricated to enable easy sliding.

A light source 65 may be disposed under optical probe P and under target assembly 30 so that light source 65 projects light L through the calibration target 45 disposed in position C and onto the optical probe P disposed within probe mount 5 and probe guide 7. Additionally, as also shown in FIG. 3, light source 65 may be attached to an optical coupler 70 that transmits light from light source 65 to one or more elements on target base 40. For example, optical coupler 70 may specifically transmit light from light source 65 to diffuser 50. Optical coupler 70 may include an optical fiber (or an optical fiber bundle) connected at both of its ends to allow for optical coupling.

The projected light L may be projected through the calibration target 45 disposed in position C and into optical probe P. The projected light travels through the calibration target 45, through the optical probe P, and out a distal end of optical probe P. The light that is projected out the distal end of optical probe P may then be measured for calibration purposes. Based upon the measured light, a user may modify calibration hinge pin 12 to correctly calibrate optical probe P.

In one example, the phantom calibration target may be disposed in position C so that the projected light is projected through the phantom calibration target and into optical probe P. The projected light travels through the phantom calibration target and through optical probe P. The light that is projected out the distal end of optical probe P is then used to calibrate optical probe P. Thus, optical probe P may be calibrated with regard to optical backscattering and/or light propagation properties using the phantom calibration target. Additionally, target assembly 30 may be slid in a direction perpendicular to the optical probe P. Therefore, target assembly 30 may be slid so that, for example, the phantom calibration target is no longer in position C and now the flat field calibration target with diffuser 50 is in position C. The projected light is then projected through the flat field calibration target and into optical probe P. The projected light travels through the flat field calibration target and through optical probe P. The light that is projected out the distal end of the optical probe P is then used to calibrate optical probe P. Thus, optical probe P may be calibrated with regard to individual throughput of optical collection elements using the flat field calibration target.

Next, target assembly 30 may again be slid so that, for example, the flat field calibration target is no longer in position C and now the mercury argon calibration target is in position C. Thus, optical probe P may be calibrated with regard to optical saturation of detection and to provide even wavelengths and/or a desired wavelength intensity using the mercury argon calibration target. When the white calibration target is in position C, optical probe P may be calibrated with regard to intensity calibration of a light source in a desired wavelength range. Additionally, when the black calibration target is in position C, optical probe P may be calibrated with regard to internal reflections.

Figure 4:
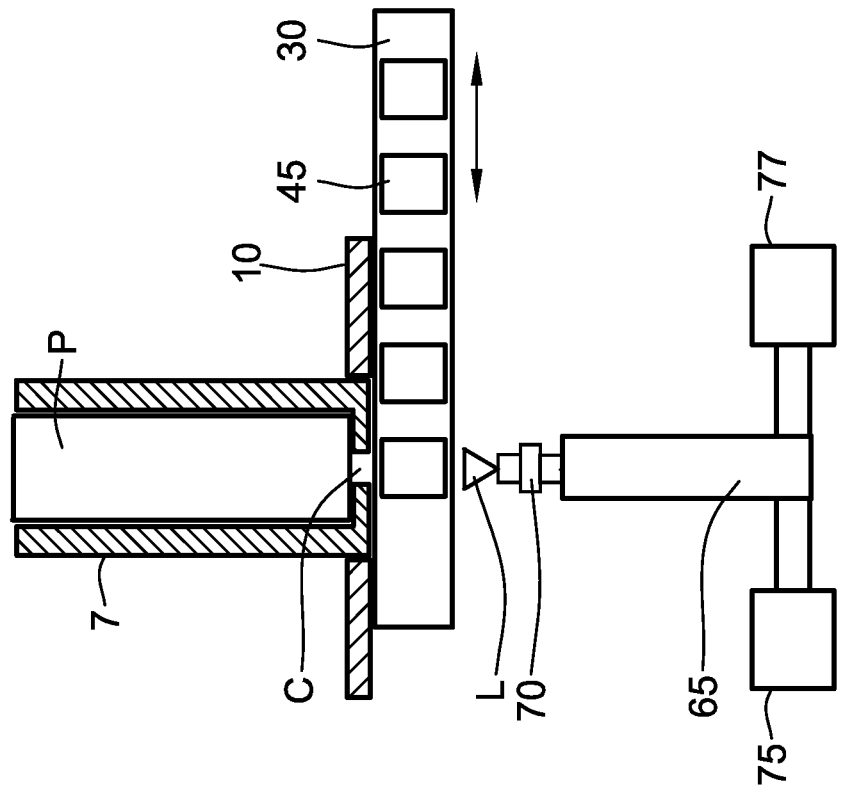
FIG. 4 illustrates the calibration system in accordance with the present disclosure.

As shown in FIG. 4, light source 65 may include a first light source 75 and a second light source 77. The separate light sources 75, 77 may provide separate and/or distinct wavelength ranges and/or spectral shape from which to calibrate optical probe P against.

A user may, in some embodiments, calibrate optical probe P for internal reflections in the presence of air by choosing the black calibration target 60 with an ambient air medium. To calibrate optical probe P for internal reflections in the presence of water, the black calibration target may be filled with a water medium or a medium of an alternative material having a refractive index substantially similar to that of water (e.g. 1.330). Water alternatives may include, for example, clear transparent silicone or clear black silicone, each simulating the optical properties of water with a substantially similar refractive index. In some embodiments, water alternatives, such as silicone, may be preferred over water because water in a black calibration target typically requires frequent replacement, and, thus, additional pump and discharge mechanisms or the like, to avoid contamination associated with use. Calibration targets filled with water alternatives, such as silicone, may be present in a solid form and, thus, reused without risk of contamination. Further, unlike liquid water, materials such as silicone provide a positive stop the probe can rest against to ensure proper placement.

Automated calibration system 1 may calibrate an optical probe that is used to detect cancerous cells. For example, the optical probe may be used to detect colon cancerous cells. Automated calibration system 1 may provide an efficient and cost-effective system for calibrating the probe. In some embodiments, the optical probe is an LEBS probe.

What is claimed is:

1. An automated calibration system for an optical probe, the system comprising:
    a probe guide configured to receive therein a fiber optic probe; and
    a target assembly attached to the probe guide, the target assembly including one or more calibration targets, the one or more calibration targets including a phantom calibration target, a white calibration target, a flat field calibration target, a mercury argon calibration target, a black calibration target, or any combination thereof,
    wherein the target assembly is slideable relative to the probe guide so that a first calibration target of the one or more calibration targets is aligned under the fiber optic probe in a first position of the target assembly, and a second calibration target of the one or more calibration targets is aligned under the fiber optic probe in a second position of the target assembly, the first calibration target being configured to be used to measure a first optical property of the fiber optic probe, the second calibration target being configured to be used to measure a second optical property of the fiber optic probe different than the first optical property of the fiber optic probe.

2. The system of claim 1, wherein the one or more calibration targets include a black calibration target having an optically absorbing surface and a water medium.

3. The system of claim 1, wherein the one or more calibration targets include a black calibration target having an optically absorbing surface and a solid non-water medium having a refractive index substantially similar to that of water.

4. The system of claim 1, wherein a shape of the black calibration target is configured to redirect partially-reflected light away from the fiber optic probe.

5. The system of claim 1, wherein the phantom calibration target is used to measure backscattering properties of the fiber optic probe.

6. The system of claim 1, wherein the white calibration target is used to measure an intensity of light in the fiber optic probe.

7. The system of claim 1, wherein the flat field calibration target is used to measure optical throughput of optical collection elements in the fiber optic probe.

8. The system of claim 1, wherein the mercury argon calibration target is used to measure an amount of optical saturation in the fiber optic probe.

9. The system of claim 1, wherein the black calibration target is used to measure internal reflections in the fiber optic probe.

10. A method of calibrating an optical probe, the method comprising:
    mounting a fiber optic probe within a probe guide;
    sliding a target assembly relative to the probe guide so that a first calibration target is aligned under the fiber optic probe;
    projecting light on the first calibration target;
    measuring a first optical property of the fiber optic probe based at least on the light projected on the first calibration target;
    sliding the target assembly relative to the probe guide so that a second calibration target is aligned under the fiber optic probe;
    projecting light on the second calibration target; and
    measuring a second optical property of the fiber optic probe based at least on the light projected on the second calibration target, the second optical property of the fiber optic probe being different than the first optical property of the fiber optic probe,
    wherein the first calibration target includes a phantom calibration target, a white calibration target, a flat field calibration target, a mercury argon calibration target, a black calibration target, or any combination thereof, or
    wherein the first calibration target includes a black calibration target having an optically absorbing surface, and either (i) a water medium or (ii) a solid non-water medium having a refractive index substantially similar to a refractive index of water.

11. The method of claim 10, wherein the second calibration target includes a phantom calibration target, a white calibration target, a flat field calibration target, a mercury argon calibration target, a black calibration target, or any combination thereof.

12. An automated calibration system for an optical probe, the system comprising:
    a probe guide configured to receive therein a fiber optic probe; and
    a target assembly attached to the probe guide, the target assembly including one or more calibration targets, the one or more calibration targets including a black calibration target having an optically absorbing surface, and either (i) a water medium or (ii) a solid non-water medium having a refractive index substantially similar to a refractive index of water,
    wherein the target assembly is slideable relative to the probe guide so that a first calibration target of the one or more calibration targets is aligned under the fiber optic probe in a first position of the target assembly, and a second calibration target of the one or more calibration targets is aligned under the fiber optic probe in a second position of the target assembly, the first calibration target being configured to be used to measure a first optical property of the fiber optic probe, the second calibration target being configured to be used to measure a second optical property of the fiber optic probe different than the first optical property of the fiber optic probe.

* * * * *